(12) United States Patent
Amann-Zalan et al.

(10) Patent No.: US 9,703,930 B2
(45) Date of Patent: Jul. 11, 2017

(54) AUTOMATIC USER-SPECIFIC SPOT BG MEASURING ROUTINE BASED ON USER CONTINUOUS BG MEASUREMENTS

(75) Inventors: Ildiko Amann-Zalan, Weinheim (DE); Bernhard Trauth, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 1193 days.

(21) Appl. No.: 13/234,195

(22) Filed: Sep. 16, 2011

(65) Prior Publication Data

US 2012/0245446 A1    Sep. 27, 2012

Related U.S. Application Data

(63) Continuation of application No. PCT/EP2010/001360, filed on Mar. 4, 2010.

(30) Foreign Application Priority Data

Mar. 16, 2009    (EP) .................................... 09003737

(51) Int. Cl.
*A61B 5/00* (2006.01)
*G06F 19/00* (2011.01)
*A61B 5/145* (2006.01)

(52) U.S. Cl.
CPC ...... *G06F 19/3481* (2013.01); *A61B 5/14532* (2013.01); *G06F 19/3437* (2013.01); *G06F 19/3406* (2013.01); *G06F 19/3456* (2013.01)

(58) Field of Classification Search
CPC .................... A61B 5/14532; G06F 19/3406

(Continued)

(56) References Cited

U.S. PATENT DOCUMENTS 6,233,471 B1 *  5/2001  Berner et al. ................. 600/345
2003/0050546 A1 *  3/2003  Desai et al. .................. 600/347

(Continued)

FOREIGN PATENT DOCUMENTS

CN    101133960 A    3/2008
CN    101305917 A    11/2008

(Continued)

OTHER PUBLICATIONS

Gross, Todd M., et al., "Performance Evaluation of the MiniMed Continuous Glucose Monitoring System During Patient Home Use", Diabetes Technology & Therapeutics, vol. 2, No. 1, (2000), pp. 49-56. XP-002545136.

*Primary Examiner* — Christian Jang
(74) *Attorney, Agent, or Firm* — Harness Dickey (57) ABSTRACT

A method and data processing device for automatically generating a user-specific measuring data recording routine for discontinuous blood glucose measurement with a blood glucose measuring device in a data processing device. The method comprises the steps of providing of process data indicating an expected continuous course of the blood glucose value of a user, in the calculation unit based on blood glucose measuring values from continuous blood glucose measurement, generating of user-specific measuring routine data, which indicate a measuring routine with user-specific measuring events for discontinuous blood glucose measurement with a blood glucose meter taking into account the process data by means of the calculation unit, and providing of the user-specific measuring routine data to the data output interface for data transmission.

13 Claims, 3 Drawing Sheets

(58) Field of Classification Search
USPC .................................. 600/345, 347, 365
See application file for complete search history.

(56) References Cited

U.S. PATENT DOCUMENTS

| | | | |
|---|---|---|---|
| 2003/0125612 A1* | 7/2003 | Fox | A61B 5/14532 600/347 |
| 2005/0038332 A1* | 2/2005 | Saidara et al. | 600/347 |
| 2007/0293790 A1 | 12/2007 | Bainczyk et al. | |
| 2008/0194934 A1 | 8/2008 | Ray et al. | |
| 2008/0269714 A1 | 10/2008 | Mastrototaro et al. | |
| 2008/0319296 A1* | 12/2008 | Bernstein et al. | 600/365 |
| 2009/0054753 A1 | 2/2009 | Robinson et al. | |

FOREIGN PATENT DOCUMENTS

| | | |
|---|---|---|
| DE | 102004057503 A1 | 6/2002 |
| GB | 2436873 A | 10/2007 |
| GB | 2443434 A | 5/2008 |
| WO | 2008/067245 A2 | 6/2008 |

\* cited by examiner

AUTOMATIC USER-SPECIFIC SPOT BG MEASURING ROUTINE BASED ON USER CONTINUOUS BG MEASUREMENTS

REFERENCE

This application is a continuation of PCT/EP2010/001360 filed Mar. 4, 2010 which is based on and claims priority to European Patent Application No. EP 09003737.5 filed Mar. 16, 2009, which are hereby incorporated by reference.

FIELD

This disclosure relates to a method of automatically generating a user-specific measurement recording routine for discontinuous blood glucose measurement with a blood glucose meter as well as a data processing device and a continuous blood glucose measuring device.

BACKGROUND

For persons suffering from diabetes, more especially diabetes mellitus, it is of particular importance to always keep their blood glucose at a certain level. The prerequisite for this is knowledge of the blood glucose level, which is therefore measured with a blood glucose meter specially designed for this purpose.

If on the basis of measured values it is found that the blood glucose level has exceeded an intended range, medication has to be administered, for example by way of injections of insulin or orally taking metformin, which is an oral anti-diabetic drug. If the intended blood glucose level range is not reached, glucose must be administered by mouth, for example through food or a drink. If the intended blood glucose range is exceeded for a longer period there is a risk of serious health complications such as blindness, kidney damage, necrosis of the limbs or neuropathy. If the specified blood glucose level is exceed briefly but considerably, this can lead to nausea, dizziness, outbreaks of sweating, or even states of confusion. It is therefore very important that a diabetic is always aware of her blood glucose status and can, if necessary, take measures by herself to prevent blood glucose levels breaking out of the intended range.

A blood glucose meter with which the blood glucose level of a diabetic is measured is known, for example from document US 2007/0293790 A1, Diagnostic system for determining substance concentrations in liquid samples, assigned to Roche Diagnostics Operations, Inc.

It is known to take blood glucose measurements in accordance with a continuous measuring routine. Such measurements are known as Continuous Glucose Measurements (CGM). Over a consecutive period the blood glucose level is measured continuously so that, for example, the course of the blood glucose level is recorded over an entire day. Evaluation of the measured blood glucose level can involve taking the average of several daily courses. In this way it is possible to record blood glucose level fluctuations dependant on the time of day. A disadvantage of continuous blood glucose measurement is that on the one hand high costs are incurred and on the other hand it is inconvenient for the diabetic, particularly due to continuously having to wear a subcutaneous sensor. In a diabetic this can lead to infections at the injection point, intolerance to plasters or skin irritations, which prevent a diabetic from wearing it permanently or over longer periods, for example several months. Continuous measurement of the blood glucose level is described, for example, in the document by Gross et al., "Performance Evaluation of the MiniMed Continuous Glucose Monitoring System During Patient Home Use", Diabetes Technology & Therapeutics, 2 (2000)49.

Discontinuous blood glucose measurements are also known, which are also referred to as Self-Measurement of Blood Glucose (SMBG) measurements and are characterised in that the blood glucose level is recorded at intervals of time in the form of individual measurements and/or individual series of measurements. In this way, with the aid of such blood glucose measurements, which are also known as structured blood glucose measurements, it is possible to measure the blood glucose level in close time relationship in connection with certain events, for example in connection with meals. Disadvantages in connection with the structured blood glucose measurements can arise if events of relevance to the diabetic's blood glucose level occur between the measuring points so that they are not detectable. In document US 2009/0054753 A1, Variable sampling interval for blood analyte determination by Robinson et al., a method is described in which based on individual blood glucose measurements as part of discontinuous measurement, the time for a following further measurement is determined in dependence on parameters. The parameters take into account environmental and patient conditions.

Thus, there is a need for a method as well as a data processing device for the automatic generation of a user-specific measurement recording routine for discontinuous blood glucose measurement with a blood glucose measuring device, allowing improved individual blood glucose level monitoring for diabetics.

SUMMARY

An optimised blood glucose measurement with a blood glucose measuring device in terms of usage and costs is disclosed. In a data processing device, during the use of process data for an expected course of the blood glucose level a measuring routine for discontinuous blood glucose measurement is automatically defined and assigned user-specific measuring routine data are provided, which on the basis of the process data take into account results in individually adapted blood glucose measurement.

The provided process data indicated an expected continuous course of the blood glucose level for a patient, usually based on measured data. From the process data time-dependent and optionally also event-dependent components are recorded which could influence the expected blood glucose course. In determining the course, the latter depends on whether event-related changes in the blood glucose level occur, which are then also recorded. Measured course data can be processed before deriving the measuring routine for discontinuous blood glucose measurement, for example as part of smoothing of the measuring curve. Individual, separate blood glucose levels can also be incorporated into the continuous curve, in order to take into consideration events influencing the blood glucose level, such as food intake, sporting activity or the administration of medication. As a result the starting point of the automatic determination of the measuring routine for discontinuous blood glucose measurement is a continuously expected course of the blood glucose level.

The historical data for the expected course of the blood glucose level of the user can take place by fully or partially transferring the data via the data input interface to the processor unit. Such historical data can include both calculated as well as experimental blood glucose level data.

However, in addition or alternatively the continuous process data can be entirely or partially generated in the processor unit itself. The process data show a continuous course for at least one contiguous period of time.

The user-specific measuring routine data, which are provided in particular for SMBG measurement, indicate measuring events, which are defined, for example, by setting out a time of day. In addition, or alternatively the measuring results can be defined in relation to another event, such as taking medication or having a meal. In connection with the user-specific measuring routine data may indicate a period of time from this event after which the blood glucose measured has to be carried out. In this way it is possible, taking into account any type of process data indicating the anticipated course of the blood glucose level of the diabetic, or properties of the blood glucose level, more particularly using previously experimentally measured parameter values, to automatically provide measuring routine data so that user-specific measuring events can be proposed for the diabetic. Blood glucose measurement with a blood glucose meter can be carried out by the diabetic herself or by another person, for example a doctor or a nurse. As the thus recorded blood glucose levels are measured times or events individually determined for the diabetic, this results in optimised and individualised monitoring of the blood glucose level of the diabetic.

With embodiments of the invention the advantages of discontinuous blood glucose measurement, also known as structured blood glucose measurement, over continuous blood glucose measurements, which in turn are usually carried out over a limited contiguous period, are retained, for example the diabetic not having to permanently wear a sensor. The costs incurred in connection with blood glucose measurements can also be minimised as the automatically generated measurement recording routine restricts the blood glucose measurements to necessary events. Compared with known discontinuous or structured blood glucose measurements, aspects of the invention result in the advantage of specific, individualised blood glucose level data recording so that the disadvantage in known discontinuous blood glucose measurement of missing blood glucose-relevant events can be avoided for the diabetic.

Whereas in known methods either the intervals between times for measurements in a discontinuous measuring routine are derived from known results of discontinuous measurements or alternatively the measurements are carried out continuously, certain embodiments of the invention combines various blood glucose measuring types, in that from continuous data for an expected course of the blood glucose level a measuring routine for discontinuous measurement is derived. To determine the measuring routine for discontinuous blood glucose measurement, it is not the event-controlled discontinuity of the SBMG measurement, as is the case in the prior art, that is used, but an expected continuous course. Surprisingly it was found that times for the measuring routine of discontinuous blood glucose measurement can be derived from such a course.

It was surprisingly found that the course of the blood glucose level can be shown in a patient-specific manner. For example, increased blood glucose measurements can be recognised as a function of the patient's "biorhythm" without food intake. In this way, not only too high or too low measurements extending as far as hypo or hyper values can be patient-specifically expected at certain times of day. In addition it was shown that depending on their biorhythm patients have periods in which the blood glucose level is particularly unstable and thus exhibits sharp fluctuations. Other examples of embodiment describe the course of the blood glucose level during the night whereby patients often exhibit hypoglycaemia while asleep. In summary it can therefore be stated that the course of the blood glucose level is patient-specifically also dominated by the physiological conditions of the patient and not only influenced in dependence on events.

In contrast to the prior art which is largely based on an event-dependent course of the blood glucose level, the proposed method allows "pattern recognition" of the course of the blood glucose, which is specific to the patient in question. Here, it is less a matter of the absolute blood glucose levels to be expected, but rather, of the relative course of blood glucose levels, which surprisingly proves to be specific to the patient, if various events influence the daily routine of the patient. Based on the knowledge that the pattern recognition of the course of blood glucose level is not only event-dependent, but is patient-specifically influenced, a prediction of the course of the blood glucose level for the patient is possible independently of events even in the case of different daily routines. More particularly, the periods of the course of the blood glucose level in which fluctuations of the blood glucose level are expected can be determined in a person-specific manner. Based on the relative blood glucose level course in the past, conclusions can therefore be drawn about the relative course of the blood glucose level in future. Advantageously, based on the relative course of blood glucose level the periods are determined for a patient which are assessed as being particularly critical as strong fluctuations occur or extreme values can be anticipated here, so that these periods can be specifically monitored. With the spot monitoring method the absolute/actual blood glucose level at the relevant time can then be determined so that specific monitoring of the blood glucose level for the periods previously assessed as critical in a patient is possible. For this, in a preferred embodiment periods are determined based in particular on the increase in the blood glucose level curve.

In addition or alternatively, periods can be determined in which the patient's blood glucose level is mainly constant so that in this way measurements can be spared at time when a constant blood glucose level can be assumed for the patient. A patient, who for example, exhibits strong fluctuations in the blood glucose level in the morning, but predominantly constant values in the afternoon, is recommended to take measurements at short intervals during the morning, but can refrain from continuous monitoring during the afternoon. In this way the measuring behaviour of the patient can be optimised and superfluous measurements avoided. In spite of the reduced number of measurements the method nevertheless allows more or less continuous monitoring of blood glucose level as by way of the specific measuring routine data an interpolation between the measuring data is possible and the course of the blood glucose level can be shown virtually continuously.

In an embodiment of the invention the user-specific measuring routine data are generated as optimised user-specific measuring routine data based on original measuring routine data. This embodiment assumes the existence of original user-specific measuring routine data which are optimised by means of the data processing device using the provided continuous process data. Thus, for example, it can be envisaged that individualised and user-specific measuring routine data already exist for a diabetic and now, for optimisation and comparison purposes, for the first time or additionally, experimental data for continuous blood glucose measurement are recorded, for instance to determine an up-to-date daily course of the blood glucose level, in order to finally determine the use-specific measuring routine on the basis of this.

In certain embodiments of the invention, the continuous process data are provided with determined process data for the user's blood glucose level which are generated in the calculation unit. In this form of embodiment the process data are fully or partially generated in the calculation unit itself, for example by means of evaluating experimental blood glucose levels.

Other embodiments of the invention envisage that influencing parameters, which indicate properties of one or more influencing parameters of relevance to the user's blood glucose level, are provided at the data input interface and the determined process data are generated in the calculation unit taking into account the influencing data. The influencing parameters can be used to fully or partially determine the expected continuous course of the blood glucose level. They can be calculated themselves by means of data processing or can be of an experimental nature. In one embodiment, they can also be used to check or alter an already existing course of the blood glucose level. The influencing parameters, which cover, in particular, previously measured data for diabetic's blood glucose level from one or more measurements, can be made available with the aid of an electronic storage medium which is connected to the data processing device via a wireless or wired data communication connection. One embodiment also envisages connection of the data processing device to a network.

In another embodiment of the invention, the user-specific measuring routine can be created in order to adjust the diabetic's measurements to a new medication or changed medication administration. In this case the influencing parameters are electronic information about the medication and/or its administration insofar as these are expected to influence the diabetic's blood glucose level. Irrespective of the type of influencing parameter data used for creating the optimised user-specific measuring routine data, with this form of embodiment it is possible to react to current changes, and several times if necessary.

In another embodiment of the invention, the influencing parameter data measured blood glucose data from continuous blood glucose measurement are provided. The blood glucose measuring data from continuous blood glucose measurements are individually determined data recorded over a longer period as part of continuous measurement, for example over several days or weeks. Such experimental data itself already indicates a final or provisionally expected continuous course of the blood glucose level or pointers thereto.

Another embodiment of the invention envisages that the influencing parameters are provided indicating properties or one or more influencing parameters selected from the following group of influencing parameters: dependency of the glucose value on the time of day, type of food, food intake, type of medication, taking of medication, person-specific influencing parameters such as age, weight, body mass index, physical activity, stress, a comorbidity and/or an acute illness. In general the influencing parameter data in electronic form can relate to individual ones of the above influencing factors or any combination thereof. This makes further individualisation of the use-specific measuring routine data possible, as a desired combination of influencing factors can be individually taken into account for the diabetic.

In an embodiment of the invention, the continuous history data with measured history data can be provided in the form of blood glucose measurements for the user which are received via the data input interface. The measured historical data can, for example, be provided as blood glucose measuring data from continuous blood glucose measurement. These are experimentally determined data recorded over a longer period as part of continuous measurement, for example over several days or weeks. In connection with this the measured blood glucose measuring data from several continuous blood glucose measurements can be averaged. The continuous blood glucose measurement can also linked to medication administration so that the influence of taking medication can be recorded and taken into account in the automatic generation of the user-specific measurement recording routine. In connection with this, measuring parameters such as the postprandial glucose excursion and the time to attaining a maximum glucose concentration, also known as time to peak, can be used. The glucose excursion is the magnitude of the postprandial glucose increase after a meal or food intake. The above parameters, which can, for example, also be evaluated within the context of studies, can be determined from the time progression of the continuous blood glucose measurement. These values themselves, or influencing parameters derived therefrom, can be used for generating the user-specific measuring routine data, more particularly also for optimising original user-specific measuring routine data.

A further embodiment of the invention envisages that the user-specific measuring routine data are generated in the blood glucose meter or are transferred via the data output interface to the blood glucose meter. Generation of the user-specific measuring routine data in the blood glucose meter itself means that the data processing device in integrated into it so that "on site" generation of the measuring routine data takes place. Alternatively the data processing device can separate from the blood glucose meter so that the user-specific measuring routine data are transferred to the blood glucose meter either via a wireless or wired data communication connection. Irrespective of whether the user-specific measuring routine data are provided in the blood glucose device or in a separate data processing device, the provision and/or outputting of the user-specific measuring routine data via the data output device can be associated with an optical and/or acoustic signal which specifically attracts the attention of the user. If the user-specific measuring routine data are present in the blood glucose meter, via a data output device of the blood glucose meter, for example a display, a signal can be sent to the user so that she is reminded once or several times of pending measurements based on the measuring data recording routine. This can be linked to an optical and/or acoustic signal output. In this way the use of the blood glucose meter is improved for the user as the diabetic is automatically informed about pending measurements in accordance with the user-specific measuring routine.

In a further embodiment of the invention, the method can also comprise the following steps: generation of control data for a measuring mode of the blood glucose meter using the user-specific measuring routine data in the blood glucose meter and controlling the measuring mode of blood glucose meter in accordance with the control data. Controlling the measuring mode of the blood glucose meter in accordance with the control data takes place with a control unit forming part of the blood glucose meter, which is, for example, a processor storage unit. Automatic controlling of the measuring mode can, for example, consist in that in accordance with the user-specific measuring routine, information is provided to the user so that she is reminded of the measuring time as part of discontinuous blood glucose measurement.

A further development of the invention can envisage that by means of the blood glucose meter blood glucose values are recorded for the user and assigned to the user-specific measuring routine data and/or the control data. This can done in such a way that measured blood glucose levels are assigned to the measuring events defined in the user-specific measuring routine data. It this way it is possible, for example, to evaluate measured blood glucose levels in accordance with the user-specific measuring data routine.

Another embodiment of the invention envisages that the user-specific measuring routine data is outputted by mean of a data output device time-delayed in accordance in relation to a temporal measuring routine and in accordance with the user-specific measuring events. As an alternative or in addition to the time-delayed output of part of the user-specific measuring routine data, a partial or complete sequence plan can be issued as an overview of the measuring events of the user-specific measuring routine. One form of embodiment envisages sending the partial or complete sequence plan in accordance with the user-specific measuring routine to the diabetic, for example via a wireless communication network to a mobile device such as a mobile phone or laptop. The provision of the user-specific measuring routine data can also be envisaged by the internet or another electronic network.

Another embodiment of the invention envisages that the user-specific measuring routine data are generated with weighting information which allocates a weighting to the user-specific measuring events of the measuring routine for discontinuous blood glucose measurement recording. The weighting, which can also be designated as prioritisation of the user-specific measurements, allows further individualisation of the user-specific blood glucose measuring routine. Initially blood glucose levels recorded in accordance with the user-specific measuring routine can be taken into account in evaluating the weighting, so that, for example, individual blood glucose levels are given a higher weighting than others. In addition or alternatively to this, one embodiment envisages formulating the signal to the user in accordance with the weighting. For example the indication for a user-specific measurement on the blood glucose meter can differ with different weightings, for instance by emitting a colour-adapted signal, with red, for example, indicating the highest priority. Also, by way of signalling on the blood glucose meter the user's attention can be drawn to higher weighted measurements several times and only once to lower weighted measurements.

Another aspect of the invention can envisage the continuous process data being analysed during the generation of user-specific measuring routine data, in order to determine periods in which at least one change to the user's blood glucose level is expected, and the user-specific measuring routine data are generated taking into account the determined periods. Taking into account the determined periods in which changes in the blood glucose level are expected means, for example, that for times assigned to the period or in temporal relationship thereto, the measuring routine suggests one or more measurements.

Alternatively or in addition, one embodiment envisages analysing of the continuous process data when generating the user-specific measuring routine data in order to determine further periods for which an essentially constant course of the blood glucose level is expected in order to derive measurement-free times for discontinuous blood glucose measurement.

In connection with the data processing device for generating a user-specific measurement recording routine for discontinuous or structured blood glucose measurement the following advantageous embodiments can be envisaged. An expedient further development of the invention envisages that the calculation unit is configured to generate the user-specific measuring routine data as optimised user-specific measuring routine data based on original user-specific measuring routine data. A further embodiment of the invention envisages that the calculation unit is configured to generate the user-specific measuring routine data with weighting information, which assigns a weighing to user-specific measurements of the measuring routine for discontinuous blood glucose measuring data recording. If can also be envisaged that the calculation unit is configured for providing the process data with determined process data for the user's blood glucose level. In one embodiment of the invention the data input interface is configured for receiving influencing parameter data showing properties of one or more influencing parameters of relevance to the user's blood glucose level, and the calculation unit is configured for generating the determined process data taking into account the influencing parameters.

In one embodiment, the data processing device can be integrated into a blood glucose meter. This embodiment envisages that the calculation unit is configured for generating control data for a measuring mode using the user-specific measuring routine data. In a further embodiment if can be envisaged that the calculation unit is configured for allocating blood glucose measurements recorded for the user to the user-specific measuring routine data and/or the control data.

BRIEF DESCRIPTION OF THE DRAWINGS

Certain embodiments of the invention are described in more detail below with the reference to the following figures.

DETAILED DESCRIPTION

Figure 1:
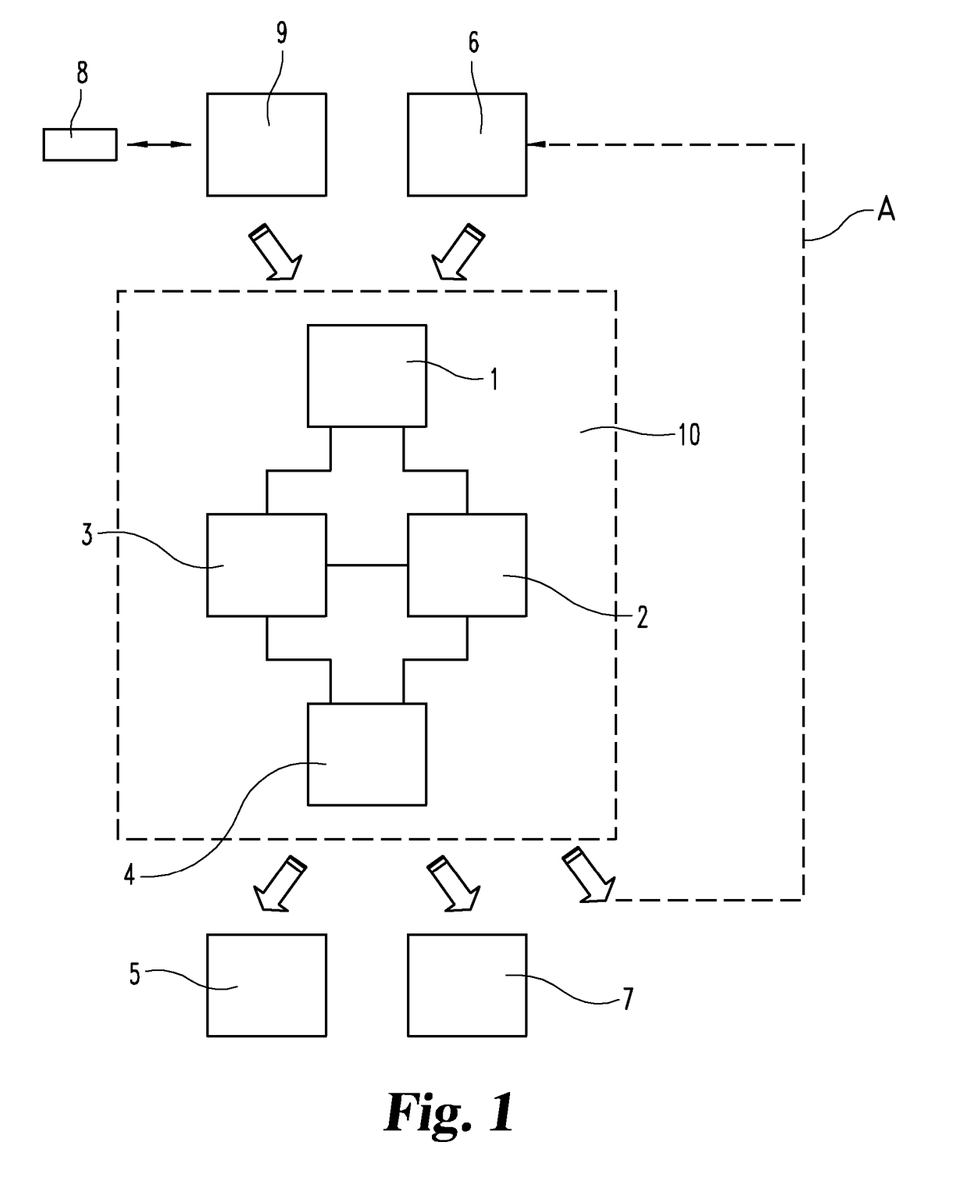
FIG. 1 shows a schematic block diagram of a data processing device for automatically generating a user-specific measurement recording routine for discontinuous blood glucose measurement with a blood glucose meter.

FIG. 1 shows a schematic view of a data processing device 10 for automatically generating a user-specific measurement recording routine for discontinuous blood glucose measurement with a blood glucose meter. Connected to a data input interface 1 is a storage device 2 as well as a calculation unit 3, which is connected to the storage device 2. The storage device 2 and the calculation unit 3 are also connected to a data output interface 4, via which electronic data can be outputted, in the case of the example of embodiment in FIG. 1 to a data output device 5 and/or a blood glucose meter 6, whereby the latter is shown in FIG. 1 by way of a dotted and dashed line A. The data output device 5, which alternatively to the embodiment in FIG. 1 can be integrated into the data processing device 10, is a display for example. Alternative or additional speech output can be provided. The data output interface 4 also makes data transfer to a storage medium 7, for example a portable storage medium, possible.

During the operation of the data processing device 10 in one form of embodiment at the data input interface 1 influencing parameter data are provided, which show properties of one or more influencing parameters or relevance to the blood glucose level of user. This can be data which already indicate fully or partially an expected course of the blood glucose level for a diabetic, for which reason these data can at least be used as part of the process data. However, the influencing parameter data can also show any parameter and its effect or influence on the blood glucose level. These influencing parameters are then processed in the calculation unit 3 in order to generate an expected course of the blood glucose level or to amend an already existing course in accordance with the influencing parameters.

In the form of embodiment shown in FIG. 1 influencing parameter data are transferred directly from the blood glucose meter 6 with which continuous blood glucose measurement has previously been carried out for the user. For data transmission a wireless or wired data communication connection can be used. Provision by way of a storage medium 8 which can read out on a reader device 9 connected to the data input interface 1 can also be envisaged. This way data from the data processing device 10 can also be outputted, whereby in this case the reading device 9 can be designed as a write-read device or can be provided as a separate write device.

The data received via the data input interface are the optionally intermediately stored in the storage device 2 and processed with the calculation unit 3 in order to generate user-specific measuring routine data which indicate a user-specific measuring routine for discontinuous blood glucose measurement recording. The data-processing in the calculation unit 3 includes the determination of a user-specific measuring routine. It can comprise determining the expected course of the blood glucose level as a preliminary stage if the process data have not already been provided. The evaluation of the continuous history data includes, for example, the determination of periods in which a change in the blood glucose level is expected in order to then propose one or more measurements for this.

The generated user-specific measuring routine data are then forwarded from the calculation unit 3 to the data output interface 4 to make them available there and, for example, to transfer them to the data output device 5. Alternatively or in addition transfer of the user-specific measuring routine data to the blood glucose meter 6 is envisaged so that the user-specific measuring routine data are available in the blood glucose meter 6. The user-specific measuring routine data can then be used there, in order, for example, to inform the user about pending measurements in accordance with the user-specific measuring routine.

The data output device 5 can, via a network into which the data processing device is integrated, be connected thereto, for example via a wireless communications network or a wired communications network, for example the internet. The network-based version has the advantage that, for example in a central data processing device, user-specific measuring routine data for a number of diabetics can be generated, which are then individually distributed via the network. In this way, a diabetic can be provided with the user-specific measuring routine data on a device used by her, which is not necessarily his/her blood glucose meter 6, but, for example a mobile phone or a computer. If desired the user can then transfer the user-specific measuring routine data from her device to the blood glucose meter 6, by means of portable electronic storage medium for example.

Figure 2:
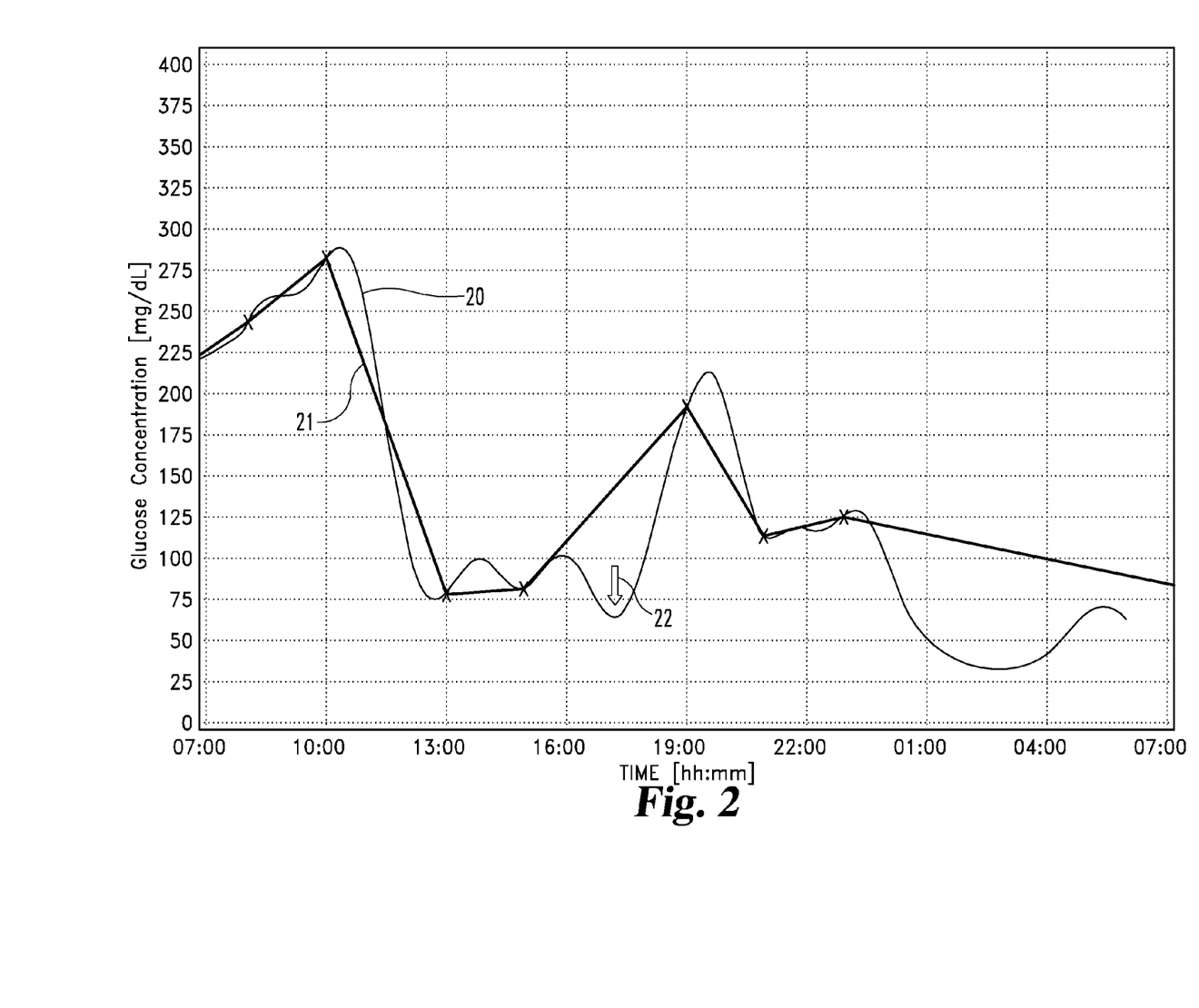
FIG. 2 shows a graphic view of the measured course of the blood glucose level of a patient in continuous blood glucose measurement for a first measuring day; and, FIG. 3 shows a graphic view of the measured course over time of the blood glucose level of a patient in continuous blood glucose measurement for a second measuring day.
Figure 3:
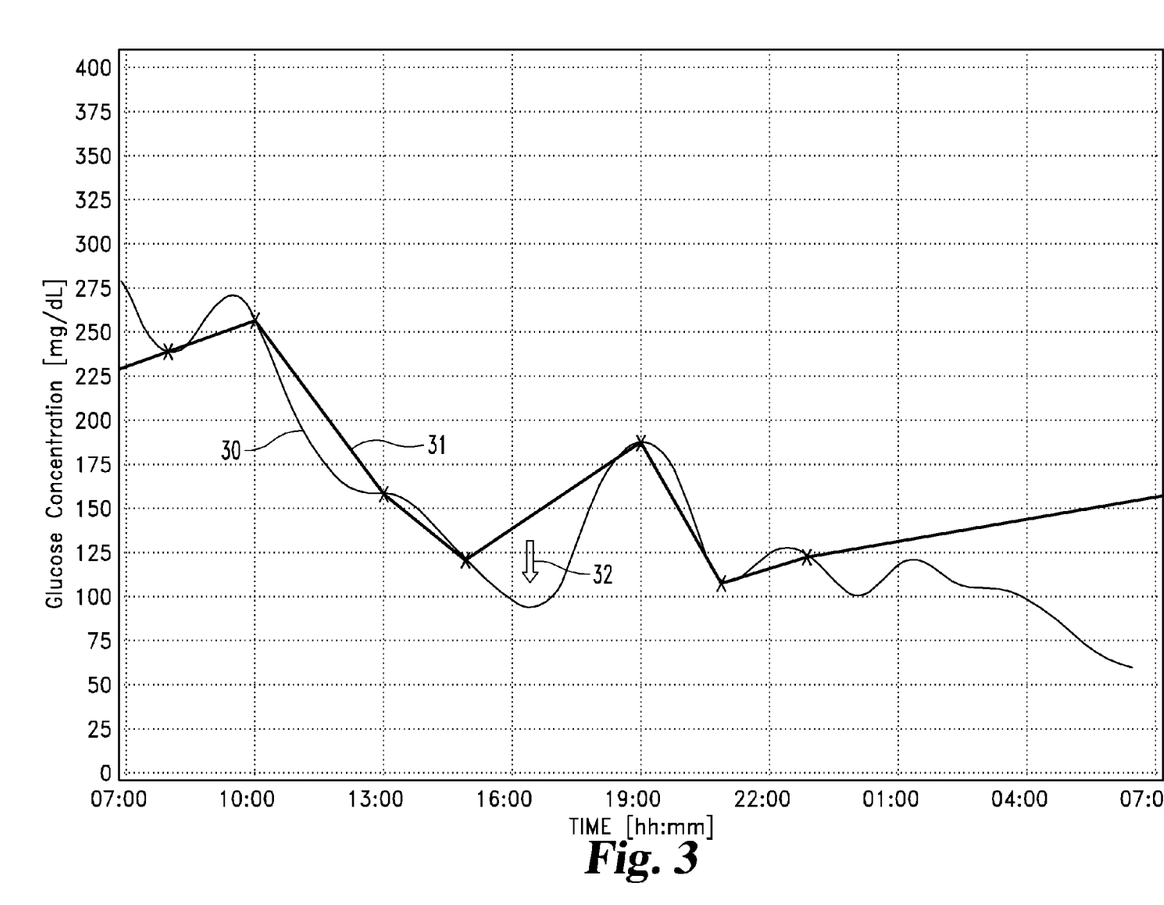

FIGS. 2 and 3 show a graphic view of the course of the blood glucose of a patient determined as part of continuous blood glucose measurement. The measured course of the blood glucose level over time for a first and a second measurement day is shown.

FIGS. 2 and 3 each show by means of a curve 20, 30 the measured course of the continuous blood glucose measurement for 24 hours, i.e. process data for the blood glucose level. Along this curve, crosses mark measuring times for a discontinuous blood glucose measurement, more particularly an SBMG measurement, which are connected in each case by means of a second curve 21, 31. This shows that in both graphs in FIGS. 2 and 4 the course of the continuous blood glucose measurement passes though a characteristic curve trough at around 17:00.

If discontinuous blood glucose measurement is then carried out in accordance with the crosses in FIGS. 2 and 3, the information about these characteristic "rogue values" of the diabetic's blood glucose level is lost. The automatic evaluation of the measured blood glucose levels with the aid of the above-described data processing device 10 now leads to user-specific measuring routine data being generated which additionally or alternatively suggest a blood glucose measurement as part of discontinuous measured for around 17:30, as for this period a change in the course of the blood glucose level has been determined. This is shown schematically in FIGS. 2 and 3 by means of arrows 22 and 32. In this way the originally selected measuring routine for discontinuous measurement is user-specifically optimised. Specifically the 7-point measurement is supplemented by one measuring point a 17:30. The measuring routine data on the basis of FIG. 2 are then provided in the information shown in Table 1, whereby the underlined measuring point 17:30 in Table 1 is the product of taking into account the measuring values for continuous blood glucose measurement.

TABLE 1

| Serial Number | Measuring Time |
|---|---|
| 1 | 8:00 |
| 2 | 10:00 |
| 3 | 13:00 |
| 4 | 15:00 |
| 5 | 17:30 |
| 6 | 19:00 |
| 7 | 21:00 |
| 8 | 23:00 |

Thus, embodiments of the automatic user-specific spot blood glucose measuring routine based on user continuous blood glucose measurements are disclosed. One skilled in the art will appreciate that the teachings can be practiced with embodiments other than those disclosed. The disclosed embodiments are presented for purposes of illustration and not limitation, and the invention is only limited by the claims that follow.

What is claimed is:

1. A method of automatically generating a user-specific measuring data recording routine for discontinuous blood glucose measurement with a blood glucose measuring device in a data processing device, which has a data input interface, a storage device, a calculation unit and a data output interface, comprising the following steps:

receiving, by the calculation unit, influencing parameter data derived from continuous blood glucose measurements of a blood glucose meter;

processing, by the calculation unit, the influencing parameter data to generate process data indicating an expected continuous course of a blood glucose value of a user;

analyzing, by the calculation unit, the process data;

determining, by the calculation unit, one or more periods in the process data within which the blood glucose values are expected to change;

setting, by the calculation unit, two or more measurement points based on the one or more periods determined;

generating, by the calculation unit, a user-specific measuring routine data that indicates a measuring routine with user-specific measuring events for discontinuous blood glucose measurement based on the two or more measurement points set, wherein the two or more measurement points define the user-specific measuring events and the user-specific measuring events are times at which a blood glucose measurement is scheduled to be taken by the user; and providing, by the calculation unit, user-specific measuring routine data to the data output interface for data transmission, where the calculation unit is implemented by computer executable instructions executed by a computer processor.

2. The method as in claim 1 further comprising, receiving, at the data input interface, influencing parameter data indicating properties of one or more influencing parameters of relevance to the blood glucose value of the user, wherein the user-specific measuring routine data is also determined based on the influencing parameter.

3. The method as in claim 2, wherein the influencing parameter data indicate properties of one or more influencing parameters selected from the group consisting of, dependency of the blood glucose value on the time of day, type of food, food intake, type of medication, medication use, person-specific influencing parameters, age, weight, body mass index, physical activity, stress, co-morbidity, and acute illness.

4. The method as in claim 1 wherein the user-specific measuring routine data are generated in the blood glucose measuring device or are transferred to the blood glucose measuring device via the data output interface.

5. The method as in claim 4, wherein the method further comprises, generating control data for a measuring mode of the blood glucose measuring device using the user-specific measuring routine data in the blood glucose measuring device; and controlling measuring mode of the blood glucose measuring device in accordance with the control data.

6. The method as in claim 4 wherein the blood glucose measuring device blood glucose values for the user are recorded and assigned to the user-specific measuring routine data and/or control data.

7. The method as in claim 1 wherein the user-specific measuring routine data are outputted by means of a data outputting device time-delayed with a temporal measuring routine and with the user-specific measuring events.

8. The method as in claim 1 wherein the user-specific measuring routine data are generated with weighting information which assigns a weighting to the user-specific measuring events of the measuring routine for discontinuous blood glucose measurement.

9. The method as in claim 1 wherein during generating the user-specific measuring routine data the process data are analyzed in order to determine further periods for which an essentially constant course of the blood sugar value is expected in order to derive measurement-free periods for the discontinuous blood glucose measurement.

10. The method as in claim 1 further comprising, a computer readable media including program instructions which when executed by a processor using software cause the processor to perform the steps of generating user-specific measuring routine data and providing the user-specific measuring routine data to the data output interface for data transmission.

11. A data processing device for generating a user-specific measuring data routine for discontinuous blood glucose measurement with a blood glucose measuring device, comprising:

a data input interface;

a storage device;

a calculation unit configured to generate a user-specific measuring routine data indicating a user-specific measuring routine for discontinuous blood glucose measurement with a blood glucose measuring device based on process data that includes blood glucose measuring values of a continuous blood glucose measurement in which a blood glucose value of the user is continuously taken such that a blood glucose level of the user is recorded over an entire day, wherein the calculation unit analyzes the process data and determines one or more periods in the process data within which the blood glucose measuring values of the continuous blood glucose measurement are expected to change and sets one or more measurement points based on the one or more periods determined, the one or more measurement points define the user-specific measuring events and the user-specific measuring events are times at which a blood glucose measurement is scheduled to be taken by the user; and a data output interface configured to transmit the user-specific measuring routine data, where the calculation unit and the data output interface are implemented by computer executable instructions executed by a computer processor of the data processing device.

12. The data processing device as in claim 11 wherein the data processing device is a blood glucose meter.

13. A method for generating a discontinuous blood glucose measurement routine by a data processing device, the method comprising:

retrieving, by a calculation unit of a blood glucose measuring device, measuring routine data for a measuring routine, where the measuring routine specifies a plurality of measuring events and each measuring event defines a time at which a discontinuous blood glucose measurement is to be taken with a blood glucose meter, receiving, by the calculation unit of the blood glucose measuring device, a time series of blood glucose measurement values from a continuous blood glucose measurement routine in which the blood glucose value of a user is continuously taken by the blood glucose measurement device, wherein the calculation unit is implemented as computer executable instructions executed by a computer processor of the data processing device;

identifying, by the calculation unit of the blood glucose measuring device, a period of time in the time series of blood glucose measurement values, where the blood glucose values of the user change during the identified time period;

determining, by the calculation unit of the blood glucose measuring device, a user-specific time at which a blood glucose measure is to be taken based on the identified time period generating, by the calculation unit of the blood glucose measuring device, a user-specific measuring event using the user-specific time at which a blood glucose measure is taken;

updating, by the calculation unit of the blood glucose measuring device, the measuring routine with the user-specific measuring event to form a user-specific measuring routine, wherein the user-specific measuring routine includes the plurality of measuring events and the user-specific measuring event; and transmitting, by a data processing device, the user-specific measuring routine to the blood glucose measurement device.

* * * * *